United States Patent [19]

Kimpara et al.

[11] Patent Number: 4,874,425

[45] Date of Patent: Oct. 17, 1989
:::

[54] STABLE AQUEOUS SUSPENSION CONCENTRATE COMPOSITIONS

[75] Inventors: Masaomi Kimpara, Hamamatsu; Kaiji Kawai, Toyohashi; Yukiya Tobe, Kanagawa, all of Japan

[73] Assignee: American Cyanamid Company, Stamford, Conn.

[21] Appl. No.: 867,108

[22] Filed: May 23, 1986

[51] Int. Cl.⁴ .............................................. A01N 33/04
[52] U.S. Cl. .................................. 71/121; 71/DIG. 1
[58] Field of Search ............................. 71/121, DIG. 1

[56] References Cited

U.S. PATENT DOCUMENTS

| | | | |
|---|---|---|---|
| 4,066,441 | 1/1978 | Lutz et al. | 71/121 |
| 4,082,537 | 4/1978 | Dudkowski | 71/121 |
| 4,150,969 | 4/1979 | Dudkowski | 71/121 |
| 4,461,641 | 7/1984 | Abildt et al. | 71/DIG. 1 |
| 4,488,896 | 12/1984 | Lamb et al. | 71/121 |

OTHER PUBLICATIONS

Kulkarni et al, "Rhszosphere Mycoflora of groundnut, etc", CA 98 174413 a, (1982), Merck, Iodine 1983, pp. 726–727.

*Primary Examiner*—Richard L. Raymond
*Assistant Examiner*—Amelia A. Owens
*Attorney, Agent, or Firm*—John W. Hogan, Jr.

[57] ABSTRACT

The present invention relates to aqueous suspension concentrate compositions or aqueous flowable compositions containing low-melting pesticides. The compositions of the invention maintain excelleant physical and biological stability.

4 Claims, No Drawings

STABLE AQUEOUS SUSPENSION CONCENTRATE COMPOSITIONS

BACKGROUND OF THE INVENTION

Suspension concentrate pesticidal compositions or aqueous flowable pesticidal compositions are concentrated suspensions of water-insoluble pesticides and mixtures of pesticides in an aqueous system. The present invention relates to stable such aqueous suspension concentrate compositions.

These aqueous compositions frequently contain about 10% to 80%, by weight, of a solid pesticide or mixture of solid pesticides, thereby providing a method for handling those pesticides which are relatively water-insoluble in an aqueous medium. Since these types of compositions have the desirable characteristics of a thick liquid, they may be poured or pumped. Thus, some of the problems, like dusting that is possible in solid compositions of wettable powders and granulars, are avoided. Further, these aqueous-based concentrates also have the added advantage of not requiring the use of organic solvents, often present in emulsifiable concentrates.

For these reasons, it is desirable to formulate pesticides into suspension concentrates or aqueous flowables. However, such formulations have their own problems such as gelling, caking and settling, as well as problems because of the physical and chemical characteristics of the pesticide or mixture of pesticides. For instance, the dinitroaniline, pendimethalin, is somewhat difficult to formulate and several references have tried to address these formulation problems.

The problems associated with the development of suspension concentrate compositions containing low-melting active ingredients, alone or in combination with higher melting active ingredients, are described in German Patent Application No. DE 3302648 A1. German Patent Application No. De3302648 Al tries to deal with the problems of an aqueous mixed dispersion of a low-melting active ingredient in a solvent of phthalic acid $C_1$–$C_{12}$ alkyl esters in combination with an aqueous suspension concentrate containing one or more active ingredients as an alternative to a suspension concentrate containing low-melting active ingredients, such as pendimethalin [N-(1-ethylpropyl)-2,6-dinitro-3,4-xylidine]. The reason for the alternative approach of that application is the inability to prepare stable suspension concentrates by various techniques, including those of European Patent Application No. 0 33291 2. That EPO application describes insecticidal suspension concentrate compositions of phosalone and adjuvants which may be prepared with molten insecticide.

Pendimethalin is known to exist at ambient temperatures in the form of two distinct polymorphs, a yellow microcrystalline form and an orange macrocrystalline form. U.S. Pat. Nos. 4,082,537 and 4,150,969 describe stable wettable powder compositions of pendimethalin in which pendimethalin is stabilized in the yellow crystal form, to avoid the problems encountered when the larger orange crystal form is present in such wettable powder compositions. However, attempts to prepare aqueous suspension concentrate compositions of stabilized pendimethalin by utilizing preparation methods acceptable for wettable powder compositions results in unstable aqueous suspension concentrate compositions which tend to grow larger crystals upon aging.

The present invention successfully formulates pendimethalin, as well as other pesticides with melting points less than 60° C., into stable aqueous suspension concentrate compositions. The compositions of the present invention are unique in that highly purified pesticide, such as pendimethalin in the yellow crystal form, is formulated with the specialized surfactants of this invention into stable aqueous suspension concentrate compositions or aqueous flowable compositions.

It is an object of the present invention, therefore, to provide stable aqueous suspension concentrate compositions or aqueous flowable compositions of low-melting pesticides (melting point less than 60° C.). Further, it is an additional object of the present invention to provide aqueous suspension concentrate compositions or aqueous flowable compositions of pendimethalin, wherein said pendimethalin is in the yellow microcrystalline form.

It is another object of the present invention to provide methods for preparing such stable aqueous suspension concentrate compositions or aqueous flowable compositions of pesticides with melting points less than 60° C., specifically pendimethalin.

SUMMARY OF THE INVENTION

The present invention relates to stable aqueous suspension concentrate compositions or aqueous flowable compositions comprising low-melting pesticides, with melting points less than 60° C., alone or in combination with pesticides having melting points higher than 70° C. Further, the compositions of the present invention include as one such low-melting pesticide pendimethalin in the yellow microcrystalline form.

Stable compositions of the present invention provide, on a weight to weight basis, improved aqueous flowable compositions, comprising, about 10.0% to 60.0%, pesticide; about 1.0%, to 10.0% sodium or calcium lignin sulfonate; about 0.05% to 0.5% thickening agent; about 0.05% to 1.0% thixotropic agent; about 0.1% to 1.0%, on a weight basis, antiseptic agent; and sufficient water to total the composition to 100%.

DETAILED DESCRIPTION OF THE INVENTION

The compositions of this invention are particularly effective for preparing stable aqueous suspension concentrates of pesticides having low-melting points, about 60° C. or less. Further, it has been found that if the low-melting active pesticide contains impurities, which oftentimes lower the melting point, that removal of these impurities by conventional methods, such as crystallization, washing, extraction or the like, prior to the preparation of the suspension concentrate is preferable.

Sodium or calcium lignin sulfonates suitable for use in the compositions of the present invention are conventionally found for use in the lumber chemical industry. Commercially, lignin sulfonates are available in both solid and liquid form, and either may be used in the compositions of the present invention. Some lignin sulfonates contain reductive saccharides, as well as saccharide derivatives and inorganic salts. It has been found that reductive saccharides are not preferable for this invention because they sometimes allow mold to grow and lead to caking during storage. Therefore, if present, they should be removed prior to use.

Thickening agents useful for the preparation of the compositions of the present invention generally include polysaccharide gums such as Xanthan gum. Further, sodium carboxymethyl cellulose, guar gum, gum arabic, sodium alginate, polyvinyl alcohol, and the like, may also be used.

Thixotropic agents suitable for use in the compositions of the present invention include clays and silica derivatives, with sodium montmorillonite being preferred for suspension concentrates of pendimethalin. This compound can be extracted from a natural swelling type clay by a physical/chemical process and is a natural colloidal hydrated aluminum-silicate, having the following general formula:

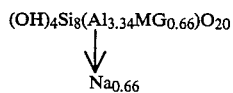

$$(OH)_4Si_8(Al_{3.34}MG_{0.66})O_{20}$$
$$\downarrow$$
$$Na_{0.66}$$

Antiseptic agents which may be used in preventing microorganism growth in the compositions of this invention include organic iodine compounds, benzoic acids, esters and salts and sodium dehydroacetate.

The following examples further illustrate the present invention but are not limitative thereof.

EXAMPLES 1–22

Preparation of aqueous suspension concentrate compositions containing pendimethalin Pendimethalin, 130.5 g (96% purity), 11.0 g of the various surfactants listed in Table I, 0.55 g of sodium montmorillonite and 121 g of water are premixed, using an Osterizer (homogenizer), for five minutes at 15±50° C. The resulting mixture is sand-ground, using a water-jacketed sand-grinder, for one to two hours. Antiseptic agents listed in Table II and 0.16 g of thickening agents listed in Table III are dissolved in 10 g of water, and the solution is then admixed with the ground mixture prepared above. The resulting aqueous suspension concentrate composition is then packaged.

Utilizing the above procedure and the surfactants, antiseptic agents and thickening agents listed in Tables I, II and III, yields the aqueous suspension concentrate compositions listed in Table IV.

TABLE I

| Designation | Surfactants Description |
|---|---|
| A-1 | P.O.E.[1] styryl phenol ether<br>Dialkyl sulfosuccinate<br>P.O.E. alkyl arlether sulfate |
| A-2 | P.O.E. stryl phenol ether<br>Dialkyl sulfosuccinate<br>P.O.E. alkyl aryether sulfate |
| A-3 | P.O.E. stryl phenyl ether polymer<br>Dialkyl sulfosuccinate |
| A-4 | Polyoxyalkylene glycol sulfate<br>P.O.E. stryl phenyl ether |
| A-5 | P.O.E. alkyl aryl ether |
| A-6 | Fatty acid polymer |
| A-7 | P.O.E. stryl phenyl ether sulfate |
| A-8 | Nonionic surfactant |
| A-9 | Nonionic surfactant |
| A-10 | Naphthalene sulfonate |
| A-11 | Lauryl sulfate |
| A-12 | Dodecyl benzene sulfonate |
| A-13 | P.O.E. octyl phenyl ether |
| A-14 | Lignin sulfonate-Ca (61%) |
| A-15 | Lignin sulfonate-Na (91%) |

[1]Polyoxyethylene

TABLE II

| Designation | Antiseptic agents Description | Composition rate |
|---|---|---|
| B-1 | Organic iodine compound | 0.2% |
| B-2 | Sodium dehydroacetate | 0.2% |
| B-3 | Sodium benzoic acid ester | 0.2% |

TABLE III

| Designation | Thickening agent Description |
|---|---|
| C-1 | Xanthan gum, polysaccharide gum |
| C-2 | CMC-Na, Sodium carboxymethyl cellulose |
| C-3 | Arabic gum, Arabin |
| C-4 | PVA, Polyvinyl alcohol |
| C-5 | Guar gum, Cyamoposis gum |
| C-6 | Alginate-Na, Sodium alginate |

TABLE IV

| No | Antiseptic agent | Formulation Surfactants | Thickening agents |
|---|---|---|---|
| 1 | B-1 | A-1 | C-1 |
| 2 | | A-2 | |
| 3 | | A-3 | |
| 4 | | A-4 | |
| 5 | | A-5 | |
| 6 | | A-6 | |
| 7 | | A-7 | |
| 8 | | A-8 | |
| 9 | | A-9 | |
| 10 | | A-10 | |
| 11 | | A-11 | |
| 12 | | A-12 | |
| 13 | | A-13 | |
| 14 | | A-14 | |
| 15 | | A-15 | |
| 16 | B-2 | A-15 | |
| 17 | B-3 | | |
| 18 | B-1 | | C-2 |
| 19 | | | C-3 |
| 20 | | | C-4 |
| 21 | | | C-5 |
| 22 | | | C-6 |

EXAMPLE 23

Stability of aqueous suspension concentrate compositions

The compositions prepared in Examples 1–22 are maintained at 45° C. in an oven for one week. Observation is made with respect to particle growth and caking, according to the methods described below:

Particle Growth

Aged samples are observed microscopically and rated according to the rating system described hereinbelow. When crystals are found, length of crystal is measured.

Caking Aged samples in glass bottle are inverted ten times and checked if caking is still evident in the bottom of the bottle afer the procedure. Then, the same rating system provided hereinbelow is used to rate caking.

Processing Characteristics Difficulties encountered during preparation of each sample are noted and recorded.

The results of these experiments, summarized in Table V, demonstrate improved stability of the compositions of the present invention.

| Rating System | |
|---|---|
| +++ | Very significant |
| ++ | Significant |
| + | Visible difference |
| ± | Slight |
| − | None |

TABLE V

| | Composition of example no | Particle growth | Caking | Difficulty in grinding |
|---|---|---|---|---|
| Comparative Compositions | 1 | +++ | ++ | D with foam |
| | 2 | +++ | ++ | D with foam |
| | 3 | +++ | ++ | D with foam |
| | 4 | +++ | ++ | D with foam |
| | 5 | +++ | ++ | D with foam |
| | 6 | +++ | ++ | D with foam |
| | 7 | +++ | ++ | D with foam |
| | 8 | ++ | +++ | D with foam |
| | 9 | +++ | ++ | D with foam |
| | 10 | ++ | +++ | D with sticky substance |
| | 11 | ++ | +++ | D with sticky substance |
| | 12 | ++ | +++ | D with sticky substance |
| | 13 | +++ | ++ | Easy |
| | 14 | ± | ± | Easy |
| | 15 | ± | − | Easy |

TABLE V-continued

| | Composition of example no | Particle growth | Caking | Difficulty in grinding |
|---|---|---|---|---|
| Compositions of the Invention | 16 | ± | − | Easy |
| | 17 | ± | − | Easy |
| | 18 | ± | ± | Easy |
| | 19 | ± | | Easy |
| | 20 | ± | − | Easy |
| | 21 | ± | ++ | Easy |
| | 22 | ± | − | Easy |

What is claimed is:

1. An aqueous flowable pesticidal concentrate composition comprising, on a weight to weight basis: about 10.0% to 60.0% pendimethalin, in the yellow microcrystalline form; about 1.0% to 10.0% sodium or calcium lignin sulfonate; about 0.05% to 0.5% thickening agent; about 0.1% to 1.0% antiseptic agent; about 0.05% to 1.0% montmorillonite; and the remainder water to total said composition to 100%.

2. A composition according to claim 1, wherein said pendimethalin has been purified to remove impurities, which lower its melting point, by crystallization, washing, extraction or mixtures thereof.

3. A composition according to claim 2, wherein said thickening agent is selected from the group consisting of sodium carboxymethyl cellulose, gum arabic, guar gum, sodium alginate or polyvinyl alcohol 4. A composition according to claim 2, wherein said thickening agent is Xanthan gum.

* * * * *